United States Patent [19]

Schwabacher

[11] 4,430,082
[45] Feb. 7, 1984

[54] HYPODERMIC SYRINGE ASSEMBLY

[75] Inventor: William Schwabacher, Wharton, N.J.

[73] Assignee: Hoffmann-La Roche Inc., Nutley, N.J.

[21] Appl. No.: 392,201

[22] Filed: Jun. 25, 1982

[51] Int. Cl.³ .............................................. A61M 5/00
[52] U.S. Cl. .................................................... 604/263
[58] Field of Search ............... 604/263, 193, 192, 187, 604/93

[56] References Cited

U.S. PATENT DOCUMENTS

| | | | |
|---|---|---|---|
| 2,671,449 | 3/1954 | Dann | 604/193 |
| 2,828,742 | 4/1958 | Ashkenaz | 604/193 |
| 4,317,446 | 3/1982 | Ambrosio et al. | 604/193 |
| 4,334,536 | 6/1982 | Pfleger | 604/263 |

Primary Examiner—John D. Yasko
Attorney, Agent, or Firm—Jon S. Saxe; Bernard S. Leon; Alan R. Stempel

[57] ABSTRACT

The present invention relates to a hypodermic syringe assembly for performing injections which has as components a flexible elastomeric protective cover into which the needle portion of a hypodermic syringe can be embedded, an inflexible hollow cylindrical sleeve which fits over the aforesaid elastomeric protective cover and a medication chamber which is bounded at its forward end by a metal needle and at its rear with an elastomeric stopper. The inflexible hollow cylindrical protective sleeve is provided at its front with connecting means so that when it is removed from the metal needle it can be attached at the rear of the medication chamber to serve as a plunger for performing injections. An additional feature of the inflexible protective sleeve is its provision with flexible gripping means which when depressed exert pressure upon the inner elastomeric protecting sleeve, thereby allowing the elastomeric protecting sleeve to be removed along with the inflexible protective sleeve. Alternatively, the inflexible hollow protective sleeve may be gripped at an inflexible portion of its length so that it may be removed while leaving the elastomeric cover disposed within in place.

3 Claims, 4 Drawing Figures

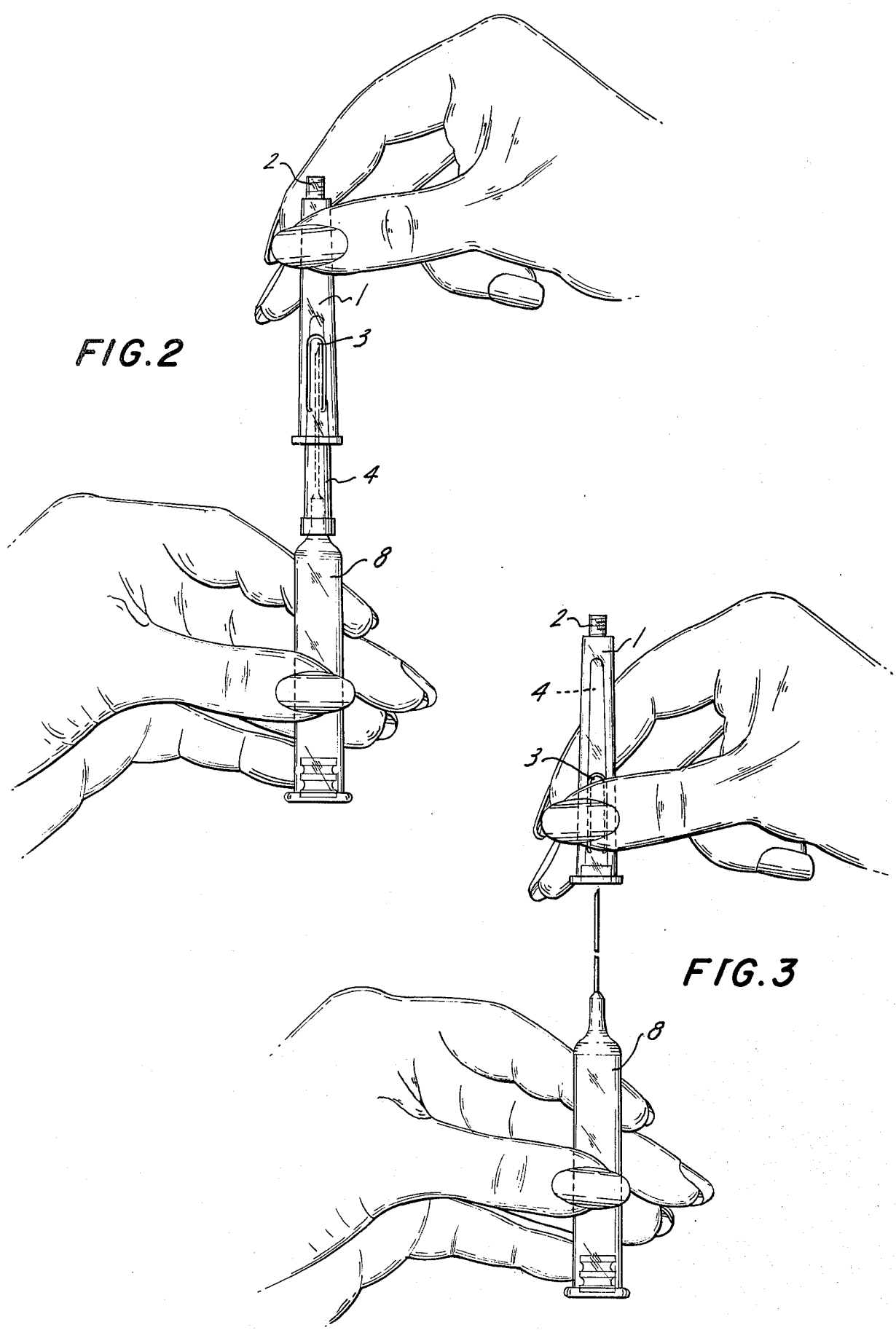

HYPODERMIC SYRINGE ASSEMBLY

FIELD OF THE INVENTION

The present invention relates to a hypodermic syringe assembly for performing injections which has as components a flexible elastomeric protective cover into which the needle portion of a hypodermic syringe can be embedded, an inflexible hollow cylindrical sleeve which fits over the aforesaid elastomeric protective cover and a medication chamber which is bounded at its forward end by a metal needle and at its rear with an elastomeric stopper.

DESCRIPTION OF THE PRIOR ART

The most frequently occurring assembly for hypodermic syringes comprises a metal needle which is attached at its rear end to a chamber which contains medication to be injected and at the rear portion of the chamber a plunger which, when depressed, forces the medication through an opening in the tip of the metal needle. Because of FDA requirements and the need to seal and sterilize the needle portion, all hypodermic syringes must have a protective cover over the needle portion for maintainence of a sterile seal. The cover is usually made of an elastomeric material or some other flexible material into which the needle can be embedded to maintain the sterile seal.

Problems have existed with the prior art hypodermic syringe assemblies. For example, in the aforementioned most frequently occuring prior art syringe arrangement, even though the needle is embedded in a flexible cover, it often gets bent and is thereby rendered useless for the performance of injections.

Additionally, from a packaging point of view, the three component assembly, i.e. needle-medication chamber-plunger, is awkward and occupies more space then optimally could be used.

Prior art syringes have sought to address the foregoing problems. For example, U.S. Pat. No. 4,317,446 to Ambrosio at al discloses a hypodermic syringe which includes a punger rod/protector which is hollowed out and affixed with threads at its end. The rod/plunger fits over an elastomeric protective sleeve into which the needle tip is embedded. This arrangement solves the problem of bent needles and additionally reduces the length of the syringe arrangement to a two component system as opposed to a three component system.

The foregoing prior art system, while it solves the problem of bent needles and more optimally utilizes packaging space, fails to provide the flexibility which is sometimes required depending upon whether it is desired to perform injections immediately after the syringe has been assembled for performing injections or whether it is desired merely to affix the plunger in place while leaving the elastomeric cover intact to maintain the sterile seal for later injections. In accordance with the present invention, an inflexible cylindrical hollow hard cover fits over an elastomeric protecting cover into which the tip of a hypodermic needle is embedded. This inflexible hard cover is affixed with attaching means at its front so that it can be attached to an elastomeric stopper at the rear of the medication chamber to serve as a plunger for performing injections.

This inflexible hollow cover is also provided with depressible gripping means which when depressed exert pressure upon the elastomeric cover disposed within, thereby gripping said cover and allowing for its removal along with the hollow inflexible cover. The hollow inflexible cover is subsequently attached to the rear of the medication chamber to serve as a plunger for performing injections. Thus the foregoing flexible gripping means facilitates situations wherein it is desired to immediately perform an injection once the sterile seal is broken and the plunger rod is affixed to the stopper at the rear of the medication chamber to serve as a plunger.

Alternatively the hollow inflexible outer protective cover may be gripped at an inflexible portion of its length and, by virtue of being in loose communication with the elastomeric cover dispossed within, may be removed while leaving the elastomeric cover in place; thereby maintaining the sterile seal while the plunger is affixed to the rear of the medication chamber. This arrangement facilitates situations wherein it is desired to prepare the syringe by affixing the inflexible sleeve as a plunger but to maintain the sterile seal for later injections. The syringe assembly of the present invention has the flexibility to accommodate both of the foregoing modes of injection.

BRIEF DESCRIPTION OF THE DRAWINGS

FIG. (1) shows the individual components of the assembly of the invention, i.e. the inflexible hollow cover affixed with flexible gripping means at the sides and with connecting means at the front, elastomeric protective cover into which the hypodermic needle of the syringe is embedded and the medication chamber which is attached to the metal needle of the hypodermic syringe at its front and at its rear elastomeric stopper which is provided with receiving means for attachment of an inflexible hollow cover to serve as a plunger for the performance of injections.

FIG. (2) shows the removal of the inflexible protective sleeve while leaving the elastomeric protective sleeve in place by gripping the inflexible protective sleeve at an inflexible portion of its length.

Figure 1:
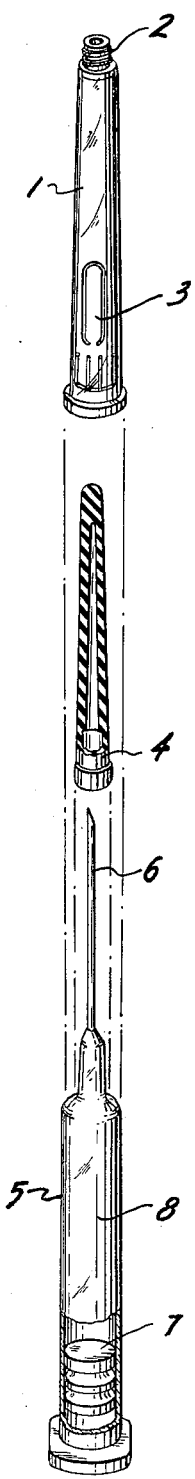
Figure 4:
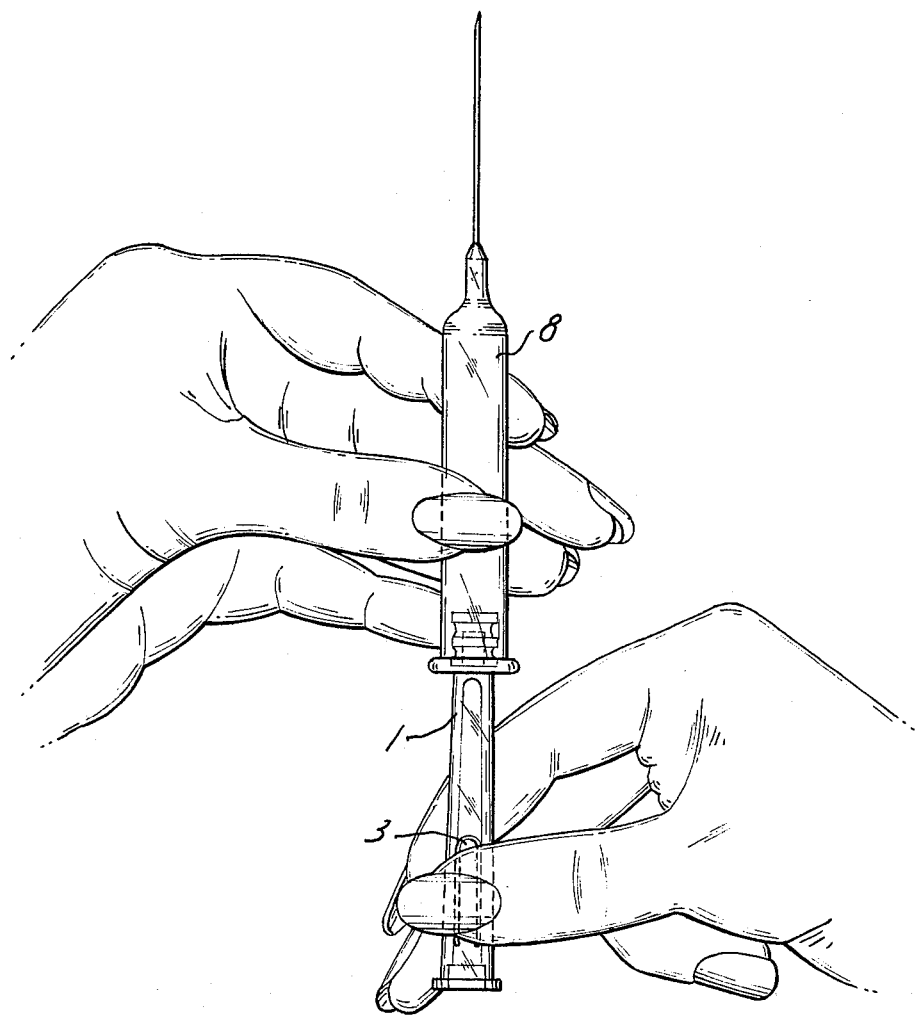

FIG. (3) shows the removal of both the inflexible outer protective sleeve and the elastomeric protective sleeve by gripping the outer protective sleeve at the flexible gripping means portion, thereby exerting pressure on the elastomeric protective sleeve disposed within the outer hollow inflexible sleeve.

FIG. (4) shows the attachment of the inflexible outer protective sleeve at the rear portion of the medication chamber of the syringe where it serves as a plunger for performing injections.

DETAILED DESCRIPTION OF THE INVENTION

The inflexible cylindrical outer sleeve (1) shown in FIG. (1) is provided with connecting means (2) at its forward end and flexible gripping means (3) at its sides. The inflexible sleeve is hollowed out so that it can fit over an elastomeric protecting sleeve (4) into which the needle portion of a hypodermic syringe may be embedded. Hypodermic syringe (5) contains a needle portion (6) at its forward end, and at its rear, end, elastomeric stopper (7) which is provided with receiving means to which connecting means (2) of inflexible protective sleeve (1) may be attached to serve as a plunger for depressing liquid contained in medication chamber (80 through the needle portion (6) of a hypodermic syringe.

By depressing gripping means (3), elastomeric protective sleeve (4) may be removed from the needle of a hypodermic syringe along with inflexible cover (1) and attachment means (2) may be connected to receiving means of elastomeric stopper (7) to serve as a plunger for performing injections. This facilitates situations where it is desired to administer an injection as soon as the syringe is assembled in an injectable arrangement.

Alternatively, inflexible sleeve (1) which is in loose communication with elastomeric sleeve (4) may be removed while leaving elastomeric sleeve (4) in place by gripping inflexible sleeve one at an inflexible portion of its length i.e., at a portion other than gripping means (3), thereby leaving elastomeric sleeve (4) in place and maintaining the sterile seal. Thus attachment means (2) of inflexible sleeve (1) may be connected to receiving means of elastomeric stopper (7), and the assembled syringe may be placed on a tray with the sterile seal remaining intact. This procedure is conveniently used for situations where it is desired to prepare the syringe for injections which are to be administered at some later point in time and thus it is necessary to maintain the sterile seal.

Inflexible sleeve (1) may be made of any thermoplastic material, which upon molding is hardened into an inflexible cast. For instance, polyethylene, polypropylene and polyvinylchloride may conveniently be used. The foregoing list of materials is intended to be exemplary and non-limiting. Flexible sleeve (4) may be made of any elastomeric material into which a hypodermic syringe needle may be embedded and which will form and maintain a sterile seal after sterilization has occured. Exemplary of materials which may be used are natural rubber, butyl rubber, and the like.

The medication chamber of the hypodermic syringe is preferably made of a clear, hard material, such as, glass, polyethylene or polypropylene.

The elastomeric stopper may be made of any flexible material which can conveniently form an air-tight closure with the walls of the medication chamber, for butyl rubber, natural rubber and the like.

The flexible gripping means can conveniently be formed by cutting a portion of inflexible cover (4) so that one or more flexible depressable tabs are formed which when depressed exert pressure upon the elastomeric protective sleeve disposed within the hollow inflexible outer protective sleeve, thereby allowing for the removal of the elastomeric inner sleeve along with the inflexible hollow outer sleeve. Alternatively, the inflexible cover may be formulated in such a manner that a selected portion is sufficiently thin to be flexible enough to allow for its depression and the gripping of the elastomeric sleeve disposed within.

The foregoing described flexible gripping means are intended to be exemplary and nonlimiting.

Attachment means at the front of the inflexible sleeve are preferably male threads which can be screwed into receiving means which are preferably female receiving threads. However, any convenient method of workably attaching the inflexible cover to the elastomeric stopper at the rear of the medication chamber is within the scope of the invention. The requirement is that the method of attachment be such that attachment means and receiving means can be brought into attached communication without exerting sufficient pressure to depress the stopper before it is intended to perform the injection and yet form a sufficiently tight attachment to allow for depression and withdrawal of the rubber stopper when the injection is being performed.

Exemplary of a suitable attachment means would be a flexible bead attachment means which fits into a lip receiving means. Also suitable would be an interrupted lug attachment means which fits into an interrupted lip receiving means such that a tight attachment is formed by a $\frac{1}{4}$ turn of the attachment means. The foregoing methods of attachment are intended to be exemplary and nonlimiting.

What is claimed is:

1. An improved hypodermic syringe assembly of the type comprising:
  (a) a medication chamber having an interior for containing liquid and first and second ends;
  (b) a needle, attached to the first end of said medication chamber, through which liquid is expelled from said chamber;
  (c) an elastomeric stopper, movably disposed within said medication chamber, movement of said stopper from said second end of said chamber toward said first end serving to expel liquid from said chamber through said needle;
  (d) a first protective sleeve into which said needle is removably embedded; and
  (e) a second protective sleeve which removably covers said first protective sleeve and, in turn, said needle, said second protective sleeve having means at one end thereof for attachment to said stopper, whereby said second protective sleeve and said stopper when so attached serve as a plunger;
    the improvement in said syringe assembly comprising the provision in said second protective sleeve of flexible means for gripping said first protective sleeve, whereby simultaneous removal of both said first and second protective sleeves from said needle are effected by removing said second protective sleeve from over said needle while inwardly deflecting said flexible gripping means in order to grip said first protective sleeve.

2. The improved syringe assembly of claim 1 wherein said flexible gripping means are tabs formed by cutting a portion of said second protective sleeve so as to form one or more flexible, inwardly deflectable tabs.

3. The improved syringe assembly of claim 2 wherein said second protective sleeve is made of polyethylene, polypropylene or polyvinylchloride.

* * * * *